(12) United States Patent
Dahl

(10) Patent No.: US 11,083,466 B2
(45) Date of Patent: Aug. 10, 2021

(54) MEDICAL COMPRESSION DEVICE

(71) Applicant: ORTRUD MEDICAL AB, Stockholm (SE)

(72) Inventor: Caroline Dahl, Stockholm (SE)

(73) Assignee: ORTRUD MEDICAL AB

( * ) Notice: Subject to any disclaimer, the term of this patent is extended or adjusted under 35 U.S.C. 154(b) by 47 days.

(21) Appl. No.: 16/630,539

(22) PCT Filed: Jul. 6, 2018

(86) PCT No.: PCT/SE2018/050745
§ 371 (c)(1),
(2) Date: Jan. 13, 2020

(87) PCT Pub. No.: WO2019/017828
PCT Pub. Date: Jan. 24, 2019

(65) Prior Publication Data
US 2021/0085335 A1    Mar. 25, 2021

(30) Foreign Application Priority Data

Jul. 17, 2017   (SE) .................................. 1700148-8

(51) Int. Cl.
*A61B 17/132* (2006.01)
*A61B 90/00* (2016.01)

(52) U.S. Cl.
CPC .. *A61B 17/1322* (2013.01); *A61B 2090/0807* (2016.02)

(58) Field of Classification Search
CPC .............. A61B 17/132; A61B 17/1322; A61B 17/1325; A61B 2090/0807; A61F 5/32
See application file for complete search history.

(56) References Cited

U.S. PATENT DOCUMENTS

| 3,613,679 A | 10/1971 | Bijou et al. |
| 4,700,715 A | 10/1987 | Levine et al. |
| 5,779,659 A * | 7/1998 | Allen ................ A61F 13/00038 602/75 |
| 6,050,967 A * | 4/2000 | Walker .............. A61F 13/00059 602/75 |

(Continued)

FOREIGN PATENT DOCUMENTS

| DE | 102015103346 A1 | 9/2016 |
| GB | 2542412 A | 3/2017 |

(Continued)

OTHER PUBLICATIONS

Extended European Search Report dated Jun. 19, 2020; European Patent Application No. 18835556.4.

(Continued)

*Primary Examiner* — Ryan J. Severson
(74) *Attorney, Agent, or Firm* — McDonald Hopkins LLC

(57) ABSTRACT

The present disclosure relates to a medical compression device (1, 1') adapted to apply a compression force to a body part (L) of a human or animal. The device comprises one or more strips intended to encircle the body part. The strip comprises a tension indicator (8, 16) adapted to inform a user when a predetermined tension is achieved, the predetermined tension correlating to a predetermined pressure on the body part. The device can be used for therapy or for diagnosis.

19 Claims, 6 Drawing Sheets

(56) References Cited

U.S. PATENT DOCUMENTS

| | | | | |
|---|---|---|---|---|
| 6,245,024 | B1* | 6/2001 | Montagnino | A61B 5/02233 600/499 |
| 6,338,723 | B1* | 1/2002 | Carpenter | A61F 13/069 602/60 |
| 7,422,256 | B2* | 9/2008 | Mueller | B66C 1/18 294/74 |
| 7,730,846 | B2* | 6/2010 | Pett | A46B 15/0002 116/212 |
| 8,900,266 | B2* | 12/2014 | Heston | A61B 17/1322 606/203 |
| 8,926,651 | B2* | 1/2015 | McDonald | A61B 17/132 606/203 |
| 10,182,825 | B2* | 1/2019 | Kirchner | A61B 17/132 |
| 10,368,877 | B2* | 8/2019 | Smith | A61B 90/08 |
| 10,478,196 | B2* | 11/2019 | Maris | A61B 17/135 |
| 2003/0144596 | A1* | 7/2003 | Tsubata | A61B 5/02233 600/500 |
| 2003/0229375 | A1* | 12/2003 | Fleischer | A61B 17/1325 606/201 |
| 2008/0072404 | A1* | 3/2008 | Wetter | B60R 22/48 24/68 R |
| 2008/0264327 | A1 | 10/2008 | Pett et al. | |
| 2009/0168612 | A1 | 7/2009 | Robin et al. | |
| 2012/0071917 | A1 | 3/2012 | McDonald et al. | |
| 2014/0018828 | A1* | 1/2014 | Foerster | A61B 17/823 606/151 |
| 2016/0317159 | A1 | 11/2016 | Smith et al. | |
| 2021/0085335 | A1* | 3/2021 | Dahl | A61B 17/1322 |

FOREIGN PATENT DOCUMENTS

| | | |
|---|---|---|
| GB | 2543485 A | 4/2017 |
| WO | 0015139 A2 | 3/2000 |
| WO | 2012088027 A2 | 6/2012 |
| WO | 2012134689 A1 | 10/2012 |

OTHER PUBLICATIONS

International Search Report and Written Opinion dated Sep. 21, 2018; International Patent Application No. PCT/SE2018/050745 filed Jul. 6, 2018. ISA/SE.

\* cited by examiner

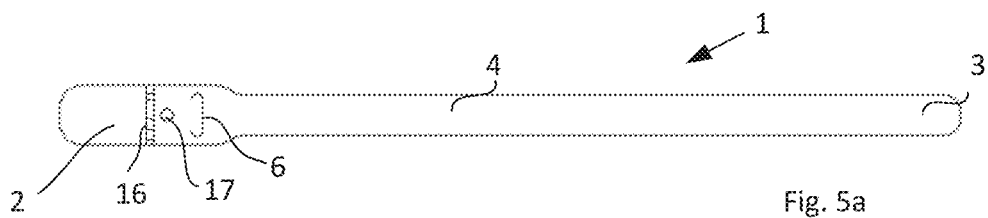
Fig. 5a
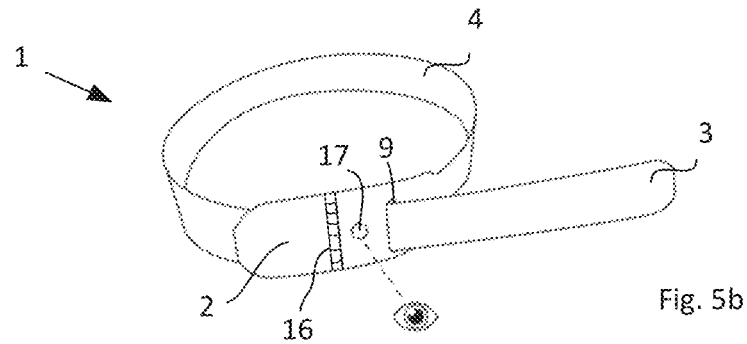
Fig. 5b
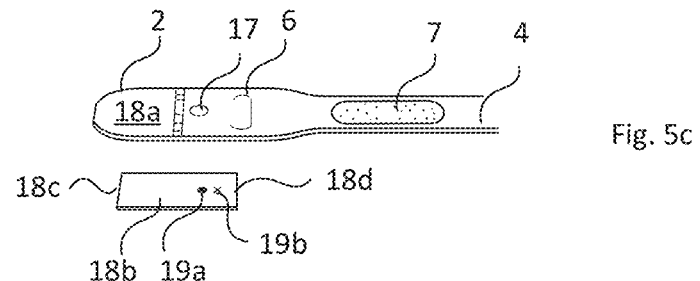
Fig. 5c
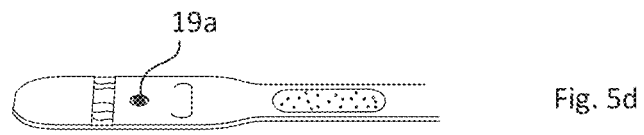
Fig. 5d
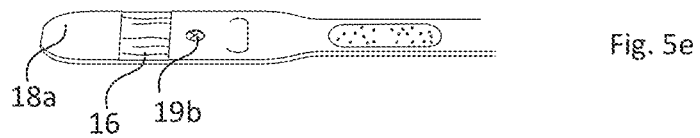
Fig. 5e
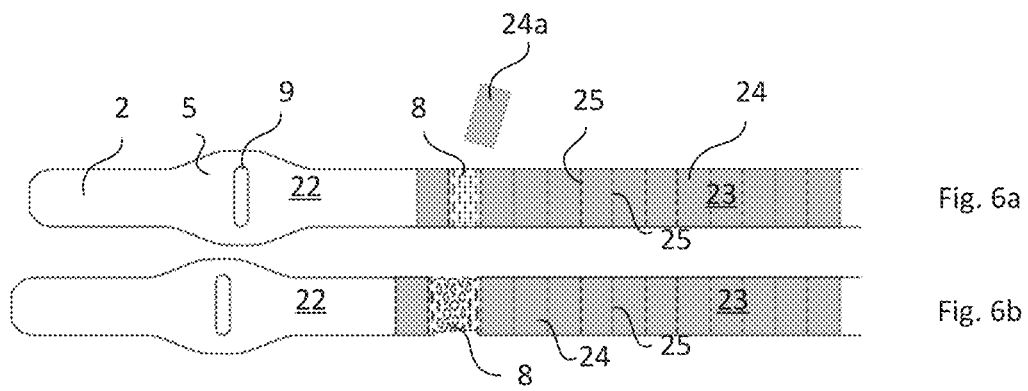
Fig. 6a
Fig. 6b

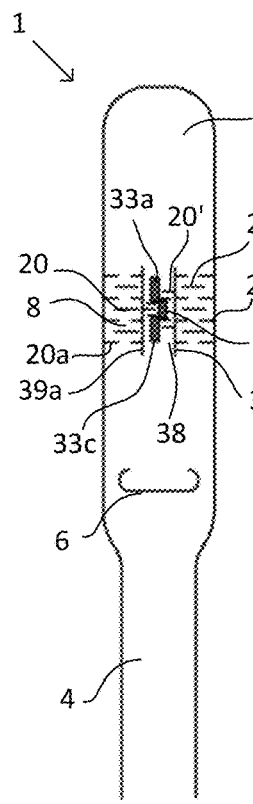
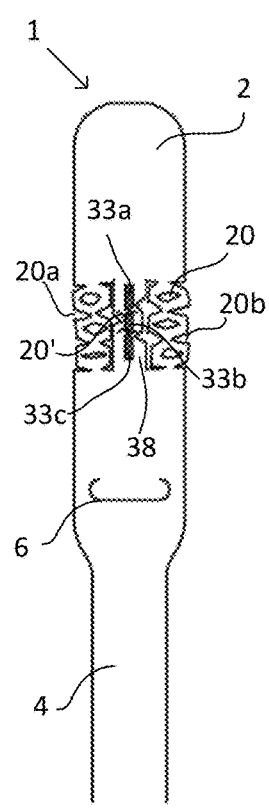
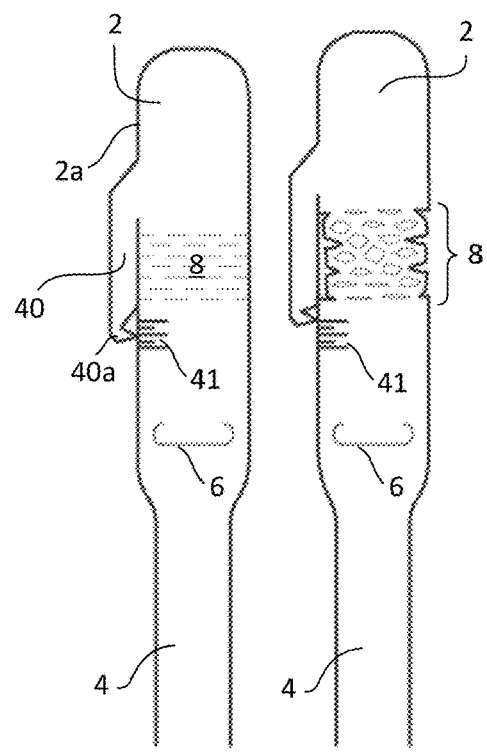
Fig. 9a    Fig. 9b    Fig. 10a    Fig. 10b
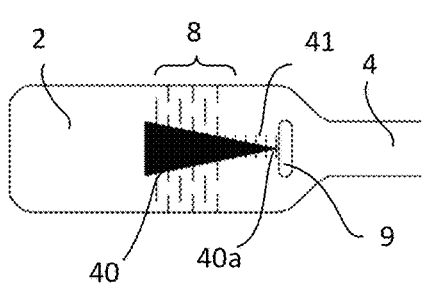
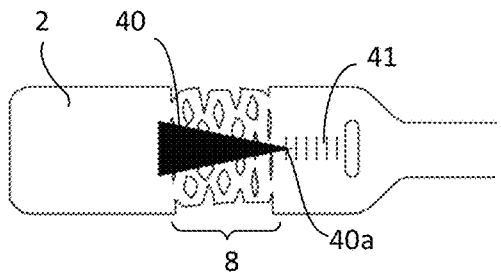
Fig. 11a    Fig. 11b
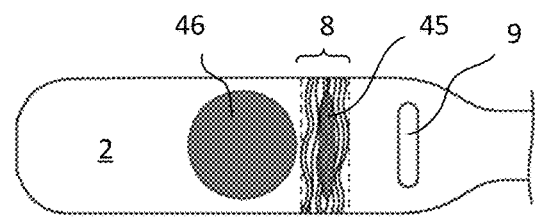
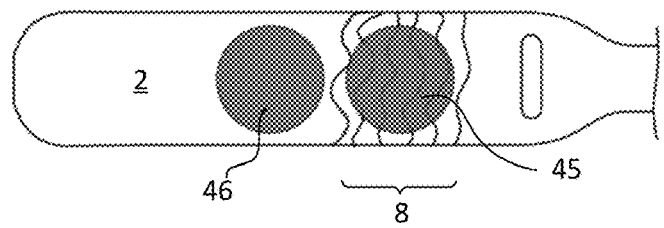
Fig. 12a
Fig. 12b

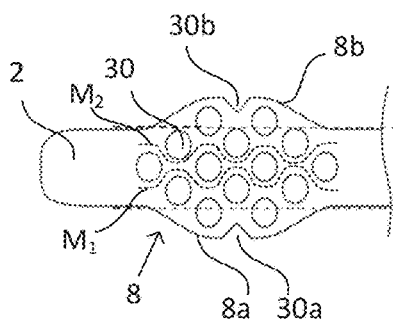
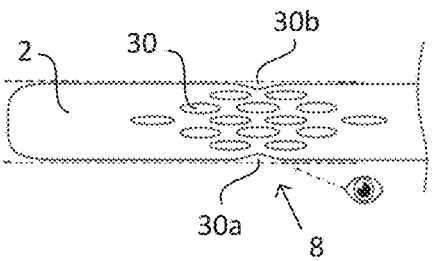
Fig. 13a
Fig. 13b
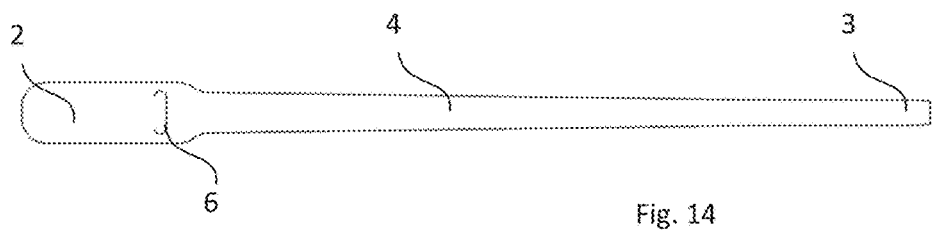
Fig. 14
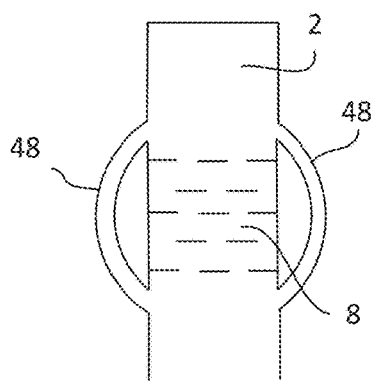
Fig. 15
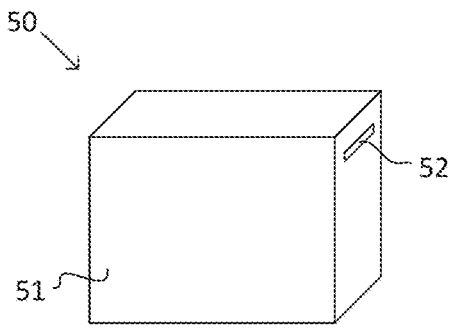
Fig. 16
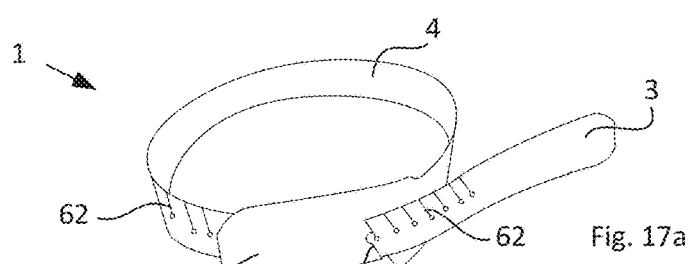
Fig. 17a
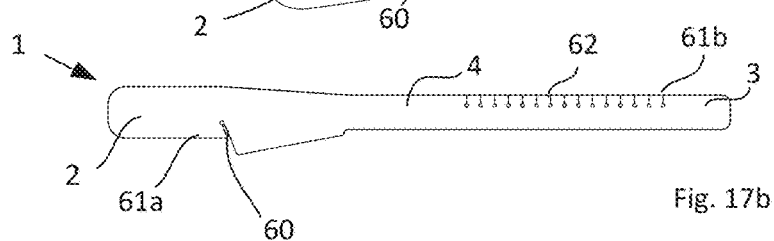
Fig. 17b

MEDICAL COMPRESSION DEVICE

CROSS-REFERENCE TO RELATED APPLICATION

This application is a 35 U.S.C. § 371 national stage application of PCT Application No. PCT/SE2018/050,745 filed on Jul. 6, 2018, entitled "MEDICAL COMPRESSION DEVICE," which claims priority to Swedish Patent Application No. 1700148-8 filed on Jul. 17, 2017, each of which are incorporated herein in their entirety by reference.

TECHNICAL FIELD

The present disclosure relates in general to a medical device for applying controlled compression to an object, in particular to a part of the body of a human or animal. The medical compression device may be a therapeutic medical compression device or a medical compression device for diagnosis.

BACKGROUND

Over half of the weight of the human body is composed of water, and blood and lymph make up a substantial part of this fluid. Disease is linked to pathological states of fluid in the body. Within the medical profession, clinicians may therefore wish to control or measure body fluid for a number of purposes.

Measurement and control of arterial blood flow is performed in order to ensure sufficient flow or limit flow. Sufficient flow needs to be ensured into for example a limb that is put into a cast, so that the affected limb has the circulation necessary for proper healing. Blood flow may also be limited temporarily, stopped temporarily, or stopped permanently for different reasons. A temporary stop may for example be necessary locally prior to surgery in order to perform planned incisions and sutures so that instruments may be inserted, progressed and used in the absence of pulsatile flow. A temporary limit to flow controls swelling in tissue after an operation such as plastic surgery. A permanent stop is necessary for example in emergency situations when a limb is severed in the field. Blood flow is commonly measured in systolic and diastolic blood pressure assessments.

Similarly, fluid accumulation needs to be measured and limited in for example conditions of lymphedema where extracellular fluid often accumulates in arms and legs of patients with damage to the lymphatic system. Further, decreased myocardial effect creates circulatory conditions where blood flow suffers and cause fluid build-up in e.g. lower limbs. Lymph and blood do not act in isolation, and pressure exerted on one system affects the other.

One example of a medical device for applying compression to a body part is a blood pressure cuff. Current blood cuffs are large and unwieldy, making them difficult to use, costly to manufacture, and difficult to keep clean.

U.S. Pat. No. 6,245,024 B1 discloses a blood pressure cuff which, when the cuff is being applied to the patient automatically indicates when the proper amount of tension in the cuff has been reached. This is achieved by a tension sensor constructed of elastomeric or elastic material comprising accordion-like ridges. The ridges include a graphic that is only fully viewable once the proper amount of tension is applied. The blood pressure cuff is however fairly bulky.

US 2003/0229375 A1 discloses a device for establishing hemostasis of an open blood vessel in a person's extremity. The device operates by application of pressure to the open vessel. The device comprises a first strip and a second flexible strip connected to the first strip. An absorbent pad is arranged around the centre of one of the strips and is supported on the strip by a compressible or flexible element that includes or cooperates with an indicator that indicates the pressure applied to the vessel by the pad.

US 2014/0018828 A1 discloses a dynamic tissue holding device for dynamically holding two tissue portions in contact with one another. The device comprises a band adapted for extending about the tissue portions to be held together and a buckle comprising a locking member, a frame and a restraining member. Application of a predetermined level of tension on the band causes the restraining member to move, thereby causing the locking member to move such that the band clamps. The device however has the disadvantage of needing a buckle.

U.S. Pat. No. 6,338,723 B1 discloses a compression device with compression measuring system. The device comprises a band made of elastic material and that can be shaped like a sleeve, wrap or garment that is sized to encircle a body part. Indicia, such as tick marks or scales, are printed on the device. The stretch of the elastic material as the device is tensioned around the body part causes increased separation of the indicia. The separation of the indicia is measured and translated to compression as a function of the circumference of the body part. The device is however a fairly complex solution to ensuring a proper compression on the body part since the indicia scales must be quite comprehensive to take into account different body configurations of patients, which in turn may make the scale difficult to read by the user and therefore increase the risk of errors. Thus, a simpler solution is desirable.

Furthermore, U.S. Pat. No. 4,700,715 discloses a device for detecting nocturnal penile erections. The device is intended to be circumferentially affixed to a flaccid penis prior to retiring at night and retrieved upon arising in the morning. The device is in the form of a band of metal foil which includes an expandable portion that will not retract once expanded. In the event of a nocturnal erection, the device will expand in response to circumferential enlargement of the penis which occurs during the erection, thereby providing information to a physician regarding the patient's ability to achieve an erection.

SUMMARY

The object of the present invention is to provide a medical device that can apply controlled compression to parts of the body for therapeutic or diagnostic purposes, and which is easy to use. The medical compression device should also preferably allow for production at low cost such that it may be used as a disposable medical compression device.

The object is achieved by a medical compression device comprising at least one elongated strip having a longitudinal central axis, a thickness and a width. The strip comprises a head portion at a first longitudinal end of the strip and a tail portion at a second longitudinal end of the strip. The strip further comprises a loop portion arranged between the head portion and the tail portion. The loop portion has a sufficient length for encircling a body part of a human or animal. The strip further comprises means for fastening overlapping portions of the strip when the loop portion is encircling a body part while applying a compressive force to the body part. Moreover, the strip comprises a tension indicator adapted to indicate when a predetermined tension in the strip, along the longitudinal axis of the strip, has been achieved. The tension indicator comprises a plurality of cuts arranged in a predetermined pattern, wherein the pattern of the plurality of cuts forms at least one meandering path of the strip material present between the cuts. At least one meandering path extends from the first longitudinal end of the tension indicator to the second longitudinal end of the tension indicator. The plurality of cuts prohibits a linear shortest available path through the strip material that links the first and second longitudinal ends of the tension indicator.

The plurality of cuts are preferably arranged in the predetermined pattern in the tension indicator such that they define at least two meandering paths of strip material between the cuts as seen along the longitudinal axis of the tension indicator. The meandering paths each extend from one longitudinal end of the tension indicator to another longitudinal end of the tension indicator. The two meandering paths may be a mirror image of one another about the longitudinal central axis of the strip. This facilitates for tension force to be evenly distributed in the tension indicator upon application.

The tension indicator is adapted to be extended along the longitudinal axis of the strip by widening of the plurality of cuts when the strip is subjected to a tension force along the longitudinal axis of the strip. The cuts and the pattern thereof in the tension indicator provide the tension indicator with a Young's modulus that is different from the Young's modulus of the rest of the elongated strip. In other words, the plurality of cuts and the pattern thereof provide the tension indicator with an elasticity that is greater than the elasticity of the rest of the elongated strip or a corresponding elongated strip that does not comprise the tension indicator. Thus, the pattern of cuts provides a controlled resistance to the tension force applied and enables the user to determine when the intended appropriate tension in the elongated strip has been achieved, the tension force correlating to pressure on the body part to which the device is applied. Thereby, the medical compression device is easy to use and reliable information is received by the user with regard the pressure achieved during use. Furthermore, the elongated strip can easily be manufactured out of a sheet of material, such a sheet optionally comprising a plurality of layers, simply by cutting, stamping or the like if desired. This leads to low production costs, which is an important issue in the case of disposable devices. A disposable medical compression device is advantageous since it avoids the risk of spreading microorganisms between patients, thereby avoiding the risk of spreading infections.

The tension indicator has a first outer edge along the longitudinal axis of the strip, and an opposing second outer edge along the longitudinal axis of the strip. Suitably, a first cut of the plurality of cuts forms a recess in the first outer edge, and a second cut of the plurality of cuts forms a recess in the second outer edge. This may in certain cases facilitate the function of the tension indicator. This also has the advantage of a medical compression device that is easy to use.

The strip may suitably be made of substantially inelastic material. This increases the control of the pressure applied since the width of the strip in contact with the body part remains essentially constant when the strip is subjected to a tension force, thereby increasing the accuracy of pressure information display associated with the tension indicator.

The strip may suitably comprise an opening configured for allowing the tail portion to pass through the opening so as to overlap with the head portion and/or the loop portion. This minimises the risk of the tension indicator being subjected to shear stress, which could otherwise affect its operation and ultimately result in less accurate pressure information display.

The strip may further comprise an intermediate portion arranged between the head portion and the loop portion. The strip may have a greater width in the intermediate portion than in the loop portion.

Such an intermediate portion may for example comprise the opening used for passing through the tail portion. Alternatively or in addition, the intermediate portion may have the purpose of accommodating the tension indicator.

The strip may optionally have a width in the loop portion that tapers towards to tail portion. This has the advantage of enabling the medical compression device to be used on body parts having different circumferences while still providing the intended pressure as determined by the tension indicator.

The strip may comprise a first strip layer and a second strip layer superposed on the first strip layer, the tension indicator arranged in the first strip layer. The second strip layer may comprise a perforation that traverses the width of the strip, said perforation arranged above the tension indicator or in the immediate vicinity thereof. This may for example have the advantage of enabling use of printed indicia on a top surface of the second strip layer, informing the user when the intended predetermined pressure has been achieved.

The second strip layer may be made of substantially inelastic material and be adhered to the first strip layer, the second strip layer comprising a plurality of perforations that traverse the width of the strip, said perforations being parallel to each other. The second strip layer may in such a case comprise a plurality of removable parts, each delimited by two adjacent perforations. The first strip layer may comprise a plurality of tension indicators; each comprising a plurality of cuts arranged in a predetermined pattern wherein the pattern forms at least one meandering path between the cuts. The tension indicators are arranged along the longitudinal axis of the loop portion such that each tension indicator is arranged below one of the removable parts of the second strip layer. Thus, when a removable part of the second strip layer is removed, the tension indicator arranged below is rendered operable while the other tension indicators remain inoperable. This has the advantage of allowing the user to select the location of the operable tension indicator.

Suitably, at least one tension indicator of the plurality of tension indicators has a different Young's modulus than a second tension indicator of the plurality of tension indicators. The Young's modulus of an individual tension indicator of the plurality of tension indicators relates to the location of the individual tension indicator along the longitudinal axis of the strip, more specifically the loop portion of the strip. Thereby, it is possible to adapt the applied tension force so that it compensates for body parts of different circumference, where body part area that is subjected to pressure may differ.

The plurality of cuts may suitably comprise a plurality of slits. Each slit may optionally be oriented substantially perpendicular to the longitudinal axis of the strip.

Suitably, the strip may further comprise an indicium or indicia adapted to visually inform the user when at least one predetermined amount of pressure is exerted by the strip on the body part. The indicium/indicia may be adapted such that one single or several levels of tension may be indicated in a single strip.

The strip may further comprise an element attached to the strip at a first end of the element and in the vicinity of the tension indicator, the element having a free end that is adapted to move in relation to the indicium or indicia of the strip as a result of extension of the tension indicator to thereby visually inform the user when predetermined pressure is exerted by the strip on the body part.

The strip may further have indicium or indicia on a top surface thereof, informing the user when the body part circumference is within an acceptable range for applying the predetermined pressure or pressure range to the body part.

According to one alternative, the strip has a greater width in the tension indicator than in adjacent parts of the strip, and the pattern of the plurality of cuts is configured to enable the width of the strip in the tension indicator to adjust to the width of the strip in adjacent parts of the strip when predetermined pressure has been achieved, so as to thereby enable the user to determined that a predetermined pressure has been achieved.

The tension indicator may be configured so that the predetermined tension correlates to a pressure on the body part where the pressure is sufficient to stop arterial blood flow in the body part. This may for example be especially suitable when the medical compression device is intended for use while performing sutures during surgery, or in emergency situations in the field.

The tension indicator may alternatively be configured so that the predetermined tension correlates to a pressure on the body part corresponding to a critical threshold value of systolic blood pressure. This is advantageous when the medical compression device should be used for diagnostic purposes. Such a critical threshold value may for example be 90 mmHg or 115 mmHg for diagnosis of hypotension or 120 mmHg, 140 mmHg or 160 mmHg for diagnosis of hypertension.

The medical compression device may comprise a plurality of the elongated strips disclosed above and one or more connection members. The connection member is configured for holding the plurality of elongated strips in relation to each other such that the elongated strips are arranged side by side as viewed in a direction perpendicular to the longitudinal axis of each elongated strip. Preferably, the elongated strips are arranged in the connection member or connection members such that elongated strips may be individually moved in relation to the connection member and other elongated strips.

The present invention also relates to a continuous band comprising a plurality of medical compression devices as disclosed above, said medical compression devices suitably consisting of the elongated strip. The medical compression devices are detachably connected to each other, one longitudinal end to another.

The present invention also relates to a dispenser comprising a box and a continuous band as disclosed above. The box further comprises an opening configured for drawing out a part of the continuous band so as to reveal a medical compression device one at a time for separation from the remainder of the elongated continuous band. The box may be sterile if desired.

The medical compression device according to the present invention may suitably be a disposable medical compression device.

BRIEF DESCRIPTION OF DRAWINGS

FIG. 5a illustrates a top view of a medical compression device according to a fourth exemplifying embodiment FIG. 5b illustrates a perspective view of the medical compression device shown in FIG. 5a before being subjected to tension.

FIG. 5c illustrates a partly exploded perspective view of a part of the medical compression device shown in FIG. 5a.

FIG. 5d illustrates a perspective view of a part of the medical compression device shown in FIG. 5a when subjected to a first tension force.

FIG. 5e illustrates a perspective view of a part of the medical compression device shown in FIG. 5a when subjected to a second tension force.

FIG. 6a illustrates a top view of a part of a medical compression device according to fifth exemplifying embodiment before being subjected to tension FIG. 6b illustrates a top view of a part of the medical compression device shown in FIG. 6a when subjected to tension FIG. 9a illustrates a top view of a part of a medical compression device according to an eight exemplifying embodiment before being subjected to tension FIG. 9b illustrates a top view of the medical compression device according to FIG. 9a when subjected to the predetermined tension FIG. 10a illustrates a top view of a part of a medical compression device according to a ninth exemplifying embodiment before being subjected to tension FIG. 10b illustrates a top view of the medical compression device according to FIG. 10a when subjected to the predetermined tension FIG. 11a illustrates a top view of a part of a medical compression device according to a tenth exemplifying embodiment before being subjected to tension FIG. 11b illustrates a top view of the medical compression device according to FIG. 11a when subjected to the predetermined tension FIG. 12a illustrates a top view of a part of a medical compression device according to an eleventh exemplifying embodiment before being subjected to tension FIG. 12b illustrates a top view of the medical compression device according to FIG. 12a when subjected to the predetermined tension FIG. 13a illustrates a top view of a part of a medical compression device according to a twelfth exemplifying embodiment before being subjected to tension FIG. 13b illustrates a top view of the medical compression device according to FIG. 13a when subjected to the predetermined tension FIG. 14 illustrates a top view of a part of a medical compression device according to a thirteenth exemplifying embodiment FIG. 15 illustrates a top view of a part of a medical compression device according to a fourteenth exemplifying embodiment FIG. 16 illustrates a perspective view of a dispenser according to one exemplifying embodiment FIG. 17a illustrates a perspective view of a medical compression device according to a fifteenth exemplifying embodiment FIG. 17b illustrates a top view of the medical compression device shown in FIG. 17a FIG. 18 illustrates a top view of a medical compression device according to a sixteenth exemplifying embodiment

DETAILED DESCRIPTION

Figure 1:
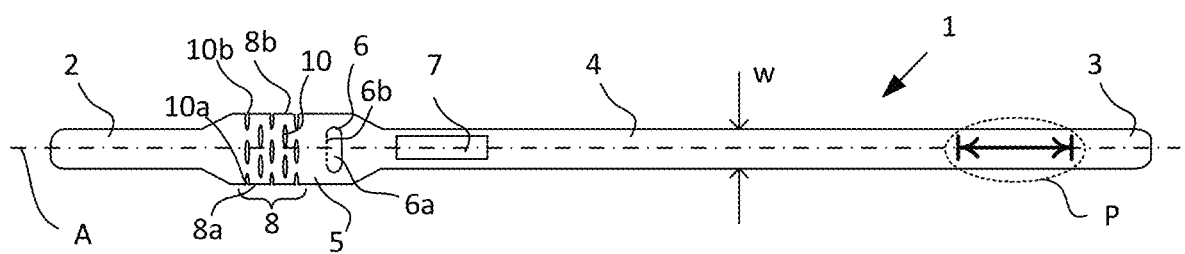
FIG. 1 illustrates a top view of a medical compression device according to a first exemplifying embodiment.

The present invention will be described below with reference to the accompanying drawings and certain exemplifying embodiments. The invention is however not limited to the embodiments shown, but may be varied within the scope of the appended claims. Moreover, the drawings shall not be considered to necessarily be drawn to scale as some features may be exaggerated in order to more clearly illustrate the features of the device(s) or the details thereof.

The term "cut" shall in the present disclosure be interpreted broadly and therefore encompasses any form of through-extending opening, such as a slit, slot, perforation, hole, aperture etc.

The term "meandering path" is in the present disclosure used in conjunction with the description of features of the tension indicator, more specifically in relation to the pattern of the plurality of cuts in the tension indicator. In the present disclosure, the term "meandering" shall be considered as something that advances or proceeds by taking a winding or indirect course with respect to a certain direction, such that the course alters with respect to the direction at least once. The term "meandering path" should therefore be considered to encompass for example a path having a sinusoidal or serpentine course, a square-shaped sinusoidal course, a zig-zag shaped course, a trapezoid-shaped sinusoidal course, a jig-saw-shaped course, etc.

Furthermore, in the present disclosure, the term "disposable" shall be considered to mean as intended for use only one time. It should however be recognised that the device may be used more than one time, if desired. The device is however preferably not intended for multiple use, such as for use on more than one patient.

Moreover, the term inelastic is used in the present disclosure when describing a property of a material. It should however be noted that no material is truly inelastic. Therefore, in the present disclosure, the term "substantially inelastic" is used. A substantially inelastic material shall be considered to mean a material which has so low elasticity that is not elongated at a tension force capable to be achieved by a human pulling the material in the plane of the material, assuming that the material is free from any cuts, macroscopic defects or the like.

The present disclosure relates to a medical compression device which may be used for therapy or for diagnosis, and which is configured to be wrapped around a body part of a human or animal so as to encircle the body part. The medical compression device is adapted for applying a controlled pressure to the body part. The medical compression device may for example be used for restricting or temporarily stop blood flow in a body part, avoid swelling of body parts or for determining critical blood pressure.

The medical compression device according to the present invention comprises an elongated strip. The medical compression device may consist solely of the strip or may comprise the strip and at least one further constituent component as will be evident from the disclosure below. For example, the device may comprise a plurality of the elongated strip.

The elongated strip has a longitudinal central axis, a thickness and a width. The thickness may be substantially constant over the whole longitudinal and transverse axis of the strip, or may be somewhat different in different parts of the strip if desired. Suitably, the thickness is substantially the same in the whole strip. The width of the strip is suitably different in different parts of the strip. However, it is also plausible, albeit less preferred that the width is substantially constant along the longitudinal axis of the strip.

The strip comprises a head portion at a first longitudinal end, a tail portion at a second longitudinal end, and a loop portion arranged between the head portion and the tail portion. The strip may optionally comprise an intermediate portion arranged between the head portion and the loop portion, if desired. Furthermore, the loop portion has a sufficient length for encircling a body part.

The strip further comprises a tension indicator adapted to indicate when a predetermined tension in the strip has been achieved when the strip is subjected to a tension force, in particular when a user pulls the strip in at least one of head portion and the tail portion. The tension indicator may be arranged in the head portion, in the intermediate portion, in the loop portion, or in the tail portion. The tension indicator has a longitudinal central axis that coincides with the longitudinal central axis of the strip. The tension indicator further comprises a first longitudinal end and a second longitudinal end. The tension indicator also comprises a plurality of cuts arranged in a predetermined pattern. The pattern may optionally comprise a plurality of different sub-patterns.

In case the pattern comprises a plurality of different sub-patterns, these sub-patterns may be separated from each other along the longitudinal axis and/or along the transverse axis of the tension indicator. In case of their being separated from each other along the transverse axis, they are suitably separated by a straight cut that runs along the longitudinal axis.

The pattern of the plurality of cuts forms at least one meandering path of the strip material present between the cuts, the meandering path extending from the first longitudinal end to the second longitudinal end of the tension indicator.

The meandering path constitutes the shortest available path of coherent strip material from a point at the first longitudinal end of the tension indicator, through the tension indicator, to the second longitudinal end of the tension indicator. Assuming a substantially inelastic material, in order for the tension indicator to extend longitudinally upon being subjected to a tension force applied along the longitudinal axis of the tension indicator, this shortest available path must be longer than the linear distance between the first and second longitudinal ends of the tension indicator. This is achieved by the plurality of cuts that prohibit a linear shortest available path, in the longitudinal direction of the tension indicator, through the strip material that links the first and second longitudinal ends of the tension indicator when the tension indicator is in its relaxed state, i.e. prior to being subjected to a tension force during use. Upon application of a tension force, the meandering path may partly or fully alter course as a result of said applied tension. In certain embodiments, the tension indicator may even elongate along the longitudinal axis such that a meandering path of the tension indicator becomes linear, i.e. parallel to the longitudinal axis of the strip, when the tension indicator is fully extended.

The plurality of cuts arranged in the predetermined pattern provides the tension indicator with an elasticity that is different from the elasticity of the rest of the strip per se. Furthermore, the predetermined pattern of the tension indicator may be configured such that it may allow, upon application of a tension force, the tension indicator to extend longer than an extension corresponding to the intended compression force to be applied to the body part by the compression device. Upon removal or reduction of the tension force, the elasticity of the tension indicator may allow the tension indicator to contract to a shorter extension.

Suitably, the pattern forms a plurality of meandering paths. The meandering paths may be identical and arranged side by side as seen along the transverse axis of the tension indicator, i.e. the paths may be parallel. However, preferably, the meandering paths may be a mirror image of one another as seen about the longitudinal central axis of the tension indicator. Furthermore, in case the cuts of the plurality of cuts are arranged in a predetermined pattern that consists of a plurality of sub-patterns (of which at least two are different from one another), the meandering paths need not necessarily have the same length.

The cuts provided in a pattern are adapted to widen along the longitudinal axis of the strip when the strip is subjected to a tension force that is applied along the longitudinal axis thereof, thus causing the tension indicator to be extended. The pattern or sub-pattern can be described as providing a desired Young's modulus of the tension indicator or, in the case of a sub-pattern, a local part of the tension indicator, which is different compared to the Young's modulus of the material of the strip as such. The Young's modulus can be selected as desired by a proper selection of the pattern or sub-pattern in terms of geometrical shape of the cuts, number of cuts, distance between the cuts, gradient(s) in density of cuts, orientation of cuts versus the longitudinal axis of the strip etc. Thus, by systematic considerations of the configuration of the tension indicator in terms of the plurality of cuts and the pattern(s) thereof, the tension indicator can be adapted to provide one or several intended predetermined levels of tension in the strip.

The cuts of the tension indicator are preferably provided in a pattern which comprises a pattern unit which is repeated both along the longitudinal axis of the strip and along the transverse axis of the strip. While repeated, the pattern units may have different sizes in different parts of the tension indicator if desired. Alternatively, the pattern units have the same size throughout the tension indicator.

The tension indicator further comprises a first outer edge that approximates the longitudinal axis of the strip, and a second outer edge that approximates the longitudinal axis of the strip. The shape of the second outer edge of the tension indicator is suitably a mirror image of the first outer edge of the tension indicator with respect to the longitudinal central axis of the strip. Optionally, the first and second outer edges may be parallel.

At least a first cut of the plurality of cuts may suitably form a recess in the first outer edge, and at least a second cut of the plurality of cuts may suitably form a recess in the second outer edge. Preferably, at least a third cut of the plurality of cuts of the tension indicator does not reach either the first or second outer edges, and therefore does not form any recess in any of the outer edges. In other words, a third cut of the plurality of cuts of the tension indicator is fully encircled by the material of the strip.

The strip of the medical compression device according to the present invention can easily be manufactured by simply cutting or stamping out the intended shape and configuration of the strip out of a sheet or band of material. Such a sheet or band may optionally comprise a plurality of individual layers and/or one or more coatings. An example of this would be to use a paper and/or plastic layer coated by pressure sensitive adhesive, such as a sticker, combined with a waxy backer layer. In combination, such strip material would enable easy adhesion by local peeling off of the sticker backer. Thus, the medical compression device can be produced at a low cost and can therefore be used as a disposable medical compression device. This has inter alia the advantage of avoiding the risk of transferring microorganisms between patients, thereby reducing the risk of transferring infections.

The strip may be made of various different substantially inelastic materials. Examples include, but are not limited to, fibre-based materials, such as paper or paper-based materials, plastic materials, or composites. In case the material of the strip is paper or paper-based, the strip may suitably be coated with a coating intended to reduce moisture absorption and/or adsorption of the strip.

Applied pressure depends on the normal force onto a surface and the area of the surface that the force is applied to. Force is given by the tension indicator, and area corresponds to the surface area of the strip in the loop region encircling the body part (i.e. the surface area in contact with the body part). While a substantially inelastic material in the loop portion ensures substantially constant width of the loop portion irrespective of tension force, body part circumference is variable across humans and animals and must therefore be accounted for in order to apply the pre-determined pressure. The present invention takes body part circumference into account in three ways as will be evident from the disclosure below:
  i. by controlling for allowed body part circumference;
  ii. by modification to the force used according to body part circumference; and/or
  iii. by modification of local strip width in the loop region to match body part circumference.

The control of allowed body part circumference, as given in (i.) above, may suitably be achieved by instructing the user on which circumference of a body part that the medical compression device may be used. This could for example be made by a marking on the medical compression device as such or the packaging thereof. Alternatively, this may also be achieved by selecting the dimensions when manufacturing the strip such that it has a length of the loop portion which is not longer than necessary for the intended circumference of the body part. For example, when intended to be used on an arm of a child or an elderly person, the loop portion may be made short. Naturally, this can be combined with a suitable marking, such as an information text.

FIG. 1 illustrates a top view of a first exemplifying embodiment of the medical compression device 1 according to the present invention. In FIG. 1, the medical compression device is shown in an as produced state before use, i.e. before being subjected to a tension force. In this exemplifying embodiment, the medical compression device consists of an elongated strip having a longitudinal central axis A, and a width w. The width w is may suitably be different at different locations along the longitudinal central axis A of the strip. The strip further comprises a head portion 2 at the first longitudinal end and a tail portion 3 at the second longitudinal end. The strip also comprises a loop portion 4 having a sufficient length to encircle a body part of a human or animal. The length of the loop portion may thus be different depending on the intended use of the medical compression device. The length of the loop portion may itself limit the applicable body part circumferences for which the device may be used to apply a pre-determined pressure. Alternatively, a print P may indicate the relevant area of the loop region that may be used, as shown in FIG. 1. The loop portion 4 is arranged between the head portion 2 and the tail portion 3.

The strip of the medical compression device further comprises an intermediate portion 5 arranged between the head portion 2 and the loop portion 4. The strip has a greater width in the intermediate portion 5 than in the loop portion 4. The intermediate portion 5 comprises a transverse cut 6 forming an opening through which the tail portion 3 and optionally a part of the loop portion 4 may pass through. The transverse cut may for example be in the form of an oval. Alternatively, it may be configured so as to form a flap 6a which may be opened about a hinge 6b formed by the material of the strip, as shown in FIG. 1.

The strip further comprises means for fastening overlapping portions of the strip when the loop portion 4 is encircling a body part and applying the intended compressive force on the body part. As shown in FIG. 1, such means for fastening may be an adhesive 7, suitably covered by a protective liner that may be peeled. The adhesive 7 is arranged on a surface of the loop portion 4 in the medical compression device shown in FIG. 1. The adhesive may however be arranged on another portion of the strip, for example the head portion or the tail portion, as desired.

When the medical compression device is to be used, the protective liner is peeled off from the adhesive 7, the loop portion 4 is wrapped around a body part of a patient such as to encircle the body part, and the tail portion 3 is threaded through the opening formed by the transverse cut 6 until the loop portion lies snug about the body part. The user may for example easily ensure that the body part circumference falls within the acceptable range by visually determining that the point where the loop portion passes through the opening formed by the cut 6 falls within the range given by the print P. Then, the head portion and the tail portion are gripped by the user and pulled in opposite directions so as to tighten the device around the body part until the loop portion applies the predetermined pressure on the body part. Thereafter, overlapping portions of the strip are fastened, while maintaining the predetermined pressure, by means of the adhesive 7.

To make sure that the predetermined pressure is achieved before locking the compression device by fastening overlapping portions as described above, the strip further comprises a tension indicator 8. As shown in FIG. 1, the tension indicator 8 may for example be arranged in the intermediate portion 5.

The tension indicator 8 comprises a plurality of cuts 10 each having a geometric shape in the form of an oval, the cuts 10 arranged in a predetermined pattern. The cuts 10 are repeated both along the longitudinal axis of the strip and along the transverse axis of the strip. The pattern of the cuts forms a plurality of meandering paths (compare with for example FIG. 2a) of the strip material present between the cuts, each meandering path extending from the first longitudinal end of the tension indicator to the second longitudinal end of the tension indicator.

The tension indicator has a first outer edge 8a which extends along the longitudinal axis of the strip, and an opposing second outer edge 8b which extends along the longitudinal axis of the strip. The first and second outer edges may for example be parallel as shown in FIG. 1. It is however plausible that the first and second outer edges are not parallel but suitably a mirror image of one another with respect to the longitudinal central axis A (compare to FIG. 13a). At least a first cut 10a of the plurality of cuts 10 reaches over the first outer edge 8a such that it forms a recess in the first outer edge. Correspondingly, at least one second cut 10b of the plurality of cuts reaches over the second outer edge 8b such that it forms a recess in the second outer edge 8b. The fact that there are cuts reaching to the outer edges of the tension indicator 8 ensures that the tension indicator can be operated despite that is has the same width as the remaining part of the intermediate portion 5. If no cuts were to reach to the longitudinally situated outer edges when the tension indicator has the same width as adjacent parts of the strip, the tension indicator would not be capable of being extended if made in inelastic material as there would be a linear, non-meandering string of material along the longitudinally situated outer edges of the tension indicator that would counteract the extension of the tension indicator.

When the compression device has been wrapped around the body part and is pulled as described above, the tension indicator 8 will be activated and the cuts will widen along the longitudinal axis of the strip, thereby extending the tension indicator along its longitudinal axis. The tension indicator's resistance to extension along the longitudinal axis correlates to the predetermined tension force intended to be achieved, which in turn corresponds to a desired pressure on the body part for a range of body part circumference. In FIG. 1, said range of the body part circumference falls within the interval designated by print P.

Figure 2A:
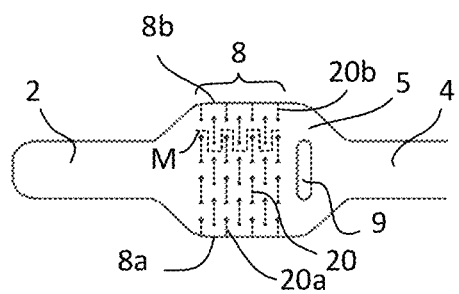
FIG. 2a illustrates a top view of a part of a medical compression device according to a second exemplifying embodiment before being subjected to a tension force.
Figure 2B:
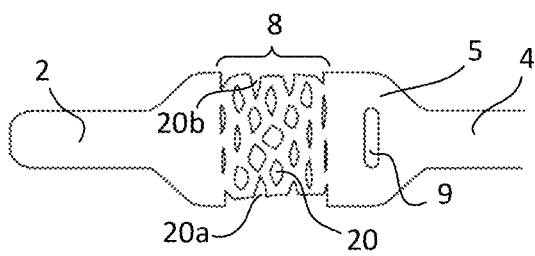
FIG. 2b illustrates a top view of the medical compression device shown in FIG. 2a when subjected to a tension force

FIG. 2a illustrates a top view of a part of a medical compression device according to a second exemplifying embodiment, before the strip is subjected to tension along the longitudinal axis thereof in the manner as described above with regard to FIG. 1. FIG. 2b illustrates a corresponding top view of the part of the medical compression device, but when subjected to tension so that the tension indicator 8 is activated. The second exemplifying embodiment differs from the exemplifying embodiment shown in FIG. 1 in that the plurality of cuts consists of a plurality of slits 20. The slits are arranged in a pattern comprising a plurality of parallel rows, each row comprising a number of slits, the major axes of which are along the transverse axis of the strip. Furthermore, the pattern is such that the slits together form a plurality of meandering paths of material, as seen along the longitudinal axis of the strip, between the slits. In FIG. 2a, one such meandering path is indicated by the dotted line M. Every second row comprises one slit 20a which forms a recess in the first outer edge 8a and another slit 20b which forms a recess in the second outer edge 8b. In the other rows, no slit reaches any one of the outer edges. As seen in FIG. 2b, when the strip is subjected to a tension force along its longitudinal axis, the slits 20 widen.

Figure 3A:
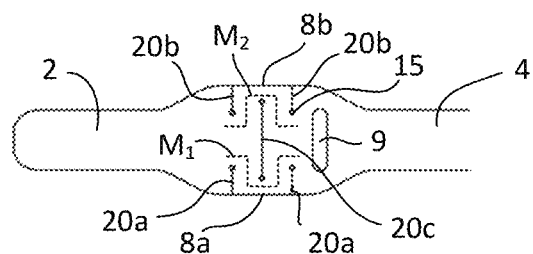
FIG. 3a illustrates a top view of a part of a medical compression device according to a third exemplifying embodiment before being subjected to a tension force.
Figure 3B:
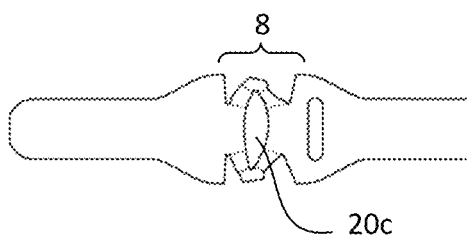
FIG. 3b illustrates a top view of the medical compression device shown in FIG. 3a when subjected to a tension force

FIG. 3a illustrates a top view of a part of a medical compression device according to a third exemplifying embodiment, before being subjected to a tension force. FIG. 3b illustrates a corresponding view but when the strip is subjected to a tension force. The third exemplifying embodiment is similar to the previously described exemplifying embodiments, but has a different pattern of the cuts. The tension indicator 8 comprises two parallel cuts in the form of slits 20a reaching the first outer edge 8a as well as two parallel cuts in the form of slits 20b reaching the second outer edge 8b so as to form recesses in the outer edges. One of the slits 20a and one of the slits 20b are located in a first plane in the transverse axis of the strip. Correspondingly, the other one of the slits 20a and the other one of the slits 20b are located in a second plane that is also located in the transverse axis of the strip. The slits 20a and 20b may in other words be considered to be provided in two parallel rows, each row consisting of two slits. Midway between the rows, each comprising two slits, the tension indicator comprises a third cut in the form of a slit 20c which does not reach any one of the outer edges 8a, 8b. The third cut is parallel to the two rows of cuts. Furthermore, each of the slits 20a, 20b, 20c may, if desired, be provided with a small circular hole 15 at the ends of the slits. Such a hole 15 has the purpose of avoiding the risk of the ends of the slits acting as break or tear initiation point due to sharpness of such ends.

The pattern of the plurality of cuts as shown in FIG. 3a forms two meandering paths between the longitudinal ends of the tension indicator. The two meandering paths are indicated in the figure by the dotted lines $M_1$, $M_2$. These two meandering paths are a mirror image of one another along the longitudinal central axes of the tension indicator and the strip.

Figure 4:
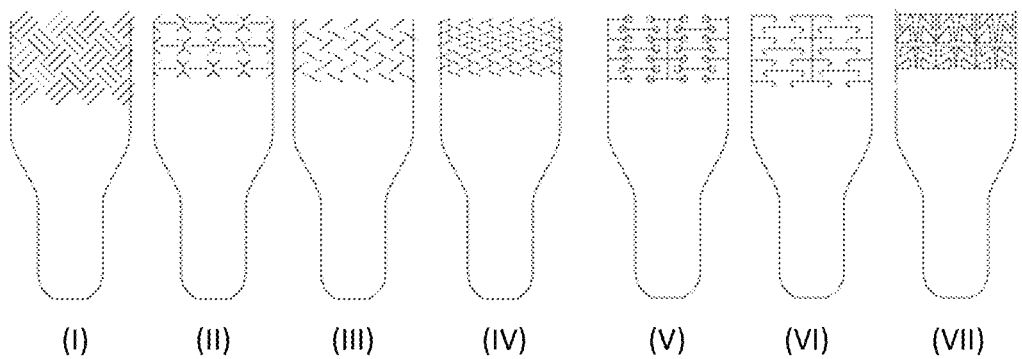
FIG. 4 illustrates examples of a plurality of cuts arranged in specific patterns in a medical compression device.

The present invention is not bound to the particular patterns of the cuts exemplified in the exemplifying embodiments shown above. For example, FIG. 4 illustrates top views of various examples of plausible patterns of cuts. The examples shown in FIG. 4 may be described as follows:

(I) Comprising cuts in the form of slits with angular major axes so as to form a "basket weave" pattern;
(II) Comprising transverse slits as well as substantially X-shaped slits separating each transverse slit from an adjacent transverse slit as seen along the transverse axis;
(III) Comprising slits with angular major axes with respect to the longitudinal axis of the strip, so as to form a substantially diamond shaped pattern;
(IV) A compressed version of (III);
(V) Corresponding to the pattern shown in FIG. 2a but further comprising a central slit situated along the longitudinal axis of the strip;
(VI) Comprising transverse substantially bracket shaped slits and a central slit situated along the longitudinal axis of the strip;
(VII) Comprising holes of complex geometrical shape(s) featuring two different sub-patterns along the longitudinal axis of the band.

The examples of FIG. 4 are merely for illustration and understanding. It will be readily understood by the skilled person that many alterations and modifications are plausible. The patterns can also be combined if desired.

FIGS. 5a to 5e illustrates a medical compression device 1 according to a fourth exemplifying embodiment. FIG. 5a illustrates a top view of the medical compression device 1 before being subjected to a tension force, and FIG. 5b illustrates a perspective view when the tail portion has been passed through an opening 9 formed by a cut 6 (see FIG. 5a), but before the strip has been subjected to a tension force. The tension indicator 16 is arranged in the head portion 2 and is shown in its relaxed state prior to extension. The tension indicator 16 is illustrated by wavy lines for sake of demonstration, but comprises in reality a plurality of cuts as previously described. As seen in FIG. 5c, which shows an exploded perspective view of a part of the device, the strip comprises an upper strip layer 18a and a lower strip layer 18b. The tension indicator is arranged in the upper strip layer 18a. The lower strip layer 18b is attached to the upper strip layer 18a at a first end 18c of the lower strip layer, and further comprises a free end 18d configured to be movable along the longitudinal axis in response to extension of the tension indicator. FIG. 5c also illustrates a possible location of the adhesive 7 for fastening overlapping portions of the device, however other locations for the adhesive are also possible.

The strip further comprises a through-opening 17 arranged between the tension indicator and the opening intended for passing through the tail portion. The through-opening 17 is intended to function with indicia 19a, 19b on the lower strip layer 18b as seen in FIG. 5c.

Before being subjected to a tension force, the strip is in a relaxed state with the tension indicator 16 remaining unextended and at least one of the indicia 19a, 19b, not being visible through the through-opening 17. This is illustrated in FIG. 5b. When the strip is subjected to a tension force, the tension indicator will extend along the longitudinal axis of the strip. At a predetermined tension, one indicium 19a is visible through the through-opening 17, as shown in FIG. 5d. If the user continues to pull the strip further, the second indicium 19b will be visible through the through-opening 17 at a second predetermined tension, as shown in FIG. 5e. Thus, the user can easily determine when the intended tension has been achieved, and if limb circumference has been compensated for, when intended pressure has been achieved. Naturally, the device may comprise more than the two indicia as illustrated in this specific exemplifying embodiment.

FIG. 6a illustrates a top view of a medical compression device according to a fifth exemplifying embodiment before being subjected to a tension force. FIG. 6b illustrates the medical compression device according to FIG. 6a when subjected to a tension force along the longitudinal axis of the strip such that the tension indicator is extended. This exemplifying embodiment is for example particularly suitable when there is a need for a medical compression device that may compensate for body parts where circumference falls within a broad spectrum. The device consists of an elongated strip having a first strip layer 22 and a second strip layer 23, the second strip layer being superposed on the first strip layer and attached thereto by means of for example an adhesive, local fusion or other means. The second strip layer may be present only in the loop portion 4, or on the whole strip from the first longitudinal end to the second longitudinal end. In FIGS. 6a and 6b, the second strip layer 23 is shown as only present in the loop portion in order to facilitate visualization of the first strip layer 22. The second strip layer 23 is made of a substantially inelastic material and will therefore not be elongated along the longitudinal axis when the strip is subjected to a tension force.

The second strip layer 23 comprises a plurality of transverse perforations 25 arranged in parallel to each other, each perforation 25 traversing the whole width of the second strip layer 23. The second strip layer 23 may optionally also be locally bonded to the first strip layer adjacent to, or at the locations where the perforations 25 are shown in FIGS. 6a and 6b, for example by local fusion of the first strip layer 22 and the second strip layer 23. The purpose of the perforation is to enable removal of a local portion 24 of the second strip layer when the compression device is to be used. This is illustrated in FIG. 6a by an already removed portion 24a of the second strip layer 23.

The first strip layer 22 comprises a number of tension indicators arranged in line along the longitudinal axis of the loop portion, or at least a part thereof. Each tension indicator is located immediately below a removable portion 24 of the second strip layer 23. Thus, upon removal of a portion 24 of the second strip layer 23 between two adjacent perforations 25, the tension indicator arranged below in the first strip layer 22 is exposed and operable. By selecting different portions 24 of the second strip layer 23 for removal, the user can select where the operable tension indicator will be situated along the longitudinal axis of the loop portion 4. In other words, the tension indicator rendered operable may be chosen based on body part circumference. The remaining tension indicators will be covered by the second inelastic strip layer 23 and thus remain inactive when the strip is subjected to the tension force. According to one additional alternative, the amount of tension indicator extension as a function of tensile stress may vary along the longitudinal axis of the loop portion 4. For example, to apply a certain pressure using a loop portion with a constant width, a smaller circumference body part requires a smaller tension than does a larger circumference body part because their radii, and thus areas that are in contact with the compression device, are different. In order to compensate for this, differential Young's moduli are adopted for the different tension indicators used for small and large radii body parts, so that a certain pressure can be applied.

Figure 7A:
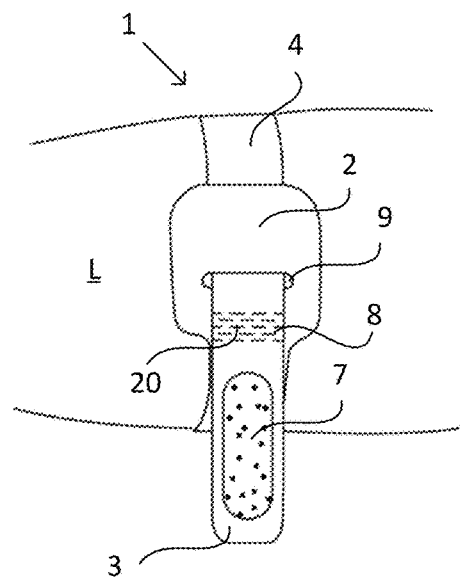
FIG. 7a illustrates a perspective view of a medical compression device according to a sixth exemplifying embodiment, when wrapped around a limb but before being subjected to tension
Figure 7B:
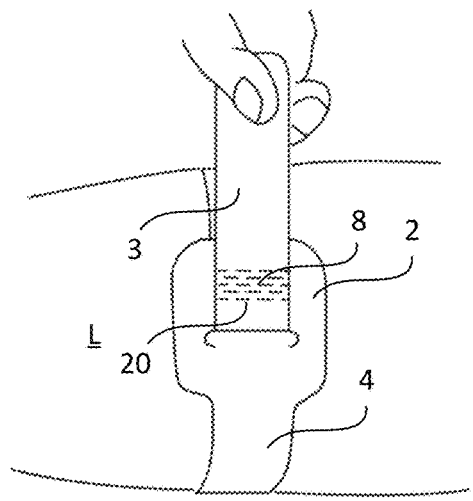
FIG. 7b illustrates a perspective view of the medical compression device according to FIG. 7a during start of pulling the device that is wrapped around a limb
Figure 7C:
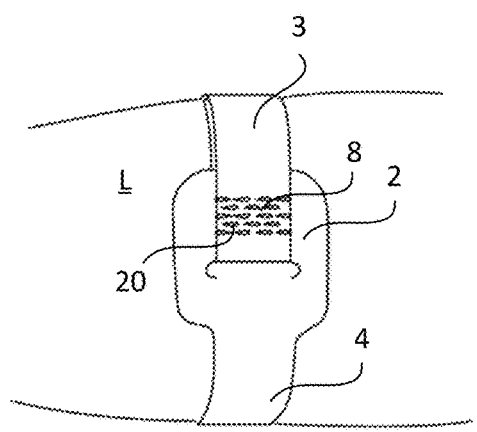
FIG. 7c illustrates a perspective view of the medical compression device according to FIG. 7a when subjected to the intended tension force and fastened with the tension force retained

FIGS. 7a to 7c illustrate a medical compression device 1 according to a sixth exemplifying embodiment and how it may be used. In the sixth exemplifying embodiment, the tension indicator 8 is arranged in the tail portion 3 of the strip. This is particularly suitable for example when it is desired to enable pulling the strip with only one hand.

FIG. 7a illustrates the device 1 when the loop portion 4 has been wrapped around a body part, such as a limb L, thereby encircling the body part. Furthermore, the tail portion has been passed through an opening 9 provided in the head portion 2 of the strip, but has not yet been subjected to any tension. The head portion 2 has a greater width than the tail portion and the loop portion such that the opening 9 is sufficiently wide for enabling the tail portion to pass through the opening 9. Moreover, the tail portion 3 comprises an adhesive 7 for enabling the tail portion to be fastened to the loop portion 4 after the intended tension has been achieved in the loop portion to apply the intended pressure to the limb L. The adhesive 7, suitably covered by a protective liner prior to use, is suitably arranged in the tail portion between the longitudinal end of the strip (at the tail portion) and tension indicator 8. The tension indicator 8 is in FIGS. 7a to 7c shown as a tension indicator comprising a plurality of cuts in the form of slits arranged in a plurality of rows. However, the tension indicator may comprise cuts arranged in a pattern in any configuration as described in the present disclosure.

FIG. 7b illustrates the device of FIG. 7a at the start of the pulling in the tail portion with the purpose of achieving an appropriate pressure on the limb L. At this stage, the cuts 20 have not yet started to widen. In other words, the tension indicator 8 has not yet been activated. When the user continues to pull the tail portion of the compression device, the tension indicator will be activated and the cuts will start to widen, thereby extending the tension indicator. Indicia (not shown) and/or elements associated with the tension indicator, may be provided to inform the user when the appropriate tension has been achieved and the tail portion can be fastened to the loop portion by means of the adhesive so as to maintain the tension achieved. FIG. 7c illustrates the device when tail portion 3 has been fastened by means of the adhesive 7 (see FIG. 7a), to the loop portion 4 where the tail portion overlaps the loop portion. As can be seen from FIG. 7c, the fact that the adhesive is provided between the longitudinal end of the strip and the tension indicator ensures that the tension indicator is maintained in the extended activated state and the user can see the tension indicator and indicia and/or indicator elements associated therewith, and thus verify that the intended pressure has been achieved and is maintained, even after overlapping portions of the strip have been fastened. In the event that retention of a specific pressure is necessary for a prolonged period of time, the tension indicator pattern may also itself be adhesive and constitute the lock. The locked strip then remains inextensible, which is useful if the Young's modulus of the pattern is a function of wear and abrasion, in which case it would be at risk of extension over time, thus lowering the pressure exerted on the limb.

Figure 8A:
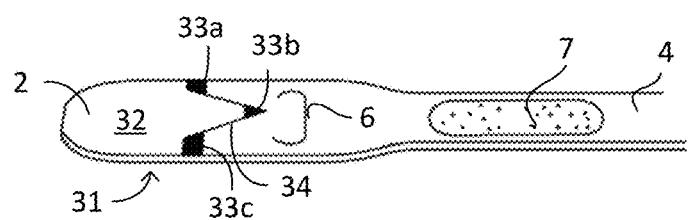
FIG. 8a illustrates a perspective view of a part of a medical compression device according to a seventh exemplifying embodiment, before being subjected to tension
Figure 8B:
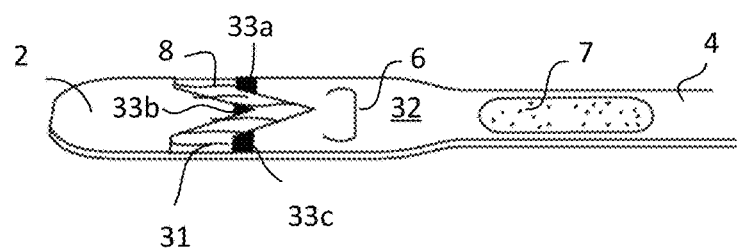
FIG. 8b illustrates a perspective view of the device shown in FIG. 8a but when subjected to a predetermined tension

FIGS. 8a and 8b illustrate a perspective view of a part of medical compression device according to a seventh exemplifying embodiment, wherein FIG. 8a illustrates the device before being subjected to a tension force and FIG. 8b illustrates the device when subjected to the intended predetermined tension force. In this exemplifying embodiment, the medical compression device consists of a strip comprising a first strip layer 31 and a second strip layer 32 superposed on the first strip layer 31. The second strip layer 32 reaches from the first longitudinal end of the strip to the second longitudinal end of the strip. Suitably, also the first strip layer reaches from the first longitudinal end of the strip to the second longitudinal end of the strip (as intended to be shown in FIGS. 8a and 8b), but this is not necessary.

The tension indicator 8 (indicated in FIG. 8b as wavy lines for demonstrating an activated state) is arranged in the first strip layer 31, and the second strip layer 32 comprises a perforation 34 that traverses from a first outer edge of the second strip layer to a second outer edge of the second strip layer so as to cross the width of the strip. In the FIGS. 8a and 8b, the perforation 34 is illustrated to traverse the second strip layer in the form of a V with the tip of the V arranged midway between the longitudinal edges of the second strip layer (i.e. the tip intersects the longitudinal central axis of the strip). However, other forms are also plausible as long as the perforation 34 reaches across the opposing outer edges of the second strip layer. The perforation 34 is configured to rupture when the strip is subjected to a tension force along the longitudinal axis of the strip and the tension indicator is activated.

It should be noted that the perforation 34 may alternatively be replaced with a permanent cut in the second strip layer arranged in the same manner as disclosed with regard to the perforation 34. In other words, the second strip layer would be divided into two separate parts without having to be ruptured when the strip is subjected to a tension force along the longitudinal axis.

The second strip layer 32 further comprises printed indicia associated with the tension indicator 8. In FIGS. 8a and 8b, this is illustrated in the form of three sub-lines 33a, 33b, 33c arranged along the transverse axis of the strip. As shown in FIG. 8b, the three sub-lines are provided such as to align into a single straight line when the appropriate tension has been achieved in the strip, as determined by the intended extension of the tension indicator made possible by the pattern formed by the plurality of cuts (not specifically illustrated in FIGS. 8a and 8b). Before the tension indicator 8 has been activated, the central sub-line 33b of the three sub-lines is provided at the tip of the V and is parallel and offset with respect to the other two sub-lines 33a, 33c, as can be seen in FIG. 8a.

FIGS. 9a and 9b each illustrate a top view of a part of a medical compression device according to an eight exemplifying embodiment, wherein FIG. 9a illustrates a state before being subjected to a tension force and FIG. 9b illustrates a state when subjected to the predetermined tension force desired. Like the exemplifying embodiment shown in FIGS. 8a and 8b, the eight exemplifying embodiment comprises indicia in the form of sub-lines intended to align into a single line when the predetermined tension force has been achieved. However, this embodiment does not rely on the presence of two separate strip layers. Furthermore, the long sides of sub-lines 33a, 33b, 33c are not oriented transversely about the strip, but longitudinally.

The device shown in FIGS. 9a and 9b consists of a strip wherein the tension indicator is arranged in the head portion 2. The tension indicator 8 comprises a plurality of cuts arranged in a predetermined pattern, wherein the cuts are in the form of transverse slits 20. The slits are provided in rows similar to what has been shown in the device illustrated in FIGS. 2a and 2b. However, in contrast to the device shown in FIGS. 2a and 2b, the tension indicator comprises a central portion 38 delimited by two parallel longitudinal cuts 39a, 39b. The central portion 38 comprises a different set of slits 20' provided in a pattern different from the slits 20 of the remaining tension indicator. The slits 20' of the central portion have the purpose of enabling the printed sub-lines 33a, 33b, 33c to align into a single line, as shown in FIG. 9b. The slits 20' thus divide the central portion 38 into parts which are movable in relation to each other as a result of the extension of the tension indicator in response to a tension force applied along the longitudinal axis of the strip.

In total, the longitudinal cuts 39a, 39b in the tension indicator 8 form three portions along the longitudinal axis of the strip; the central portion 38 and the two portions that line its periphery. Each portion contains a plurality of cuts where the slits in a first row is somewhat offset to the slits of an adjacent row, such that the joining material forms a meandering path of material (a connection) along the longitudinal axis of each portion in the tension indicator 8. Each portion has two associated longitudinal edges, and at least a first slit forms a recess in the first edge (c.f. 20a of the leftmost peripheral portion) and at least a second slit forms a recess in the second outer edge (c.f. 20b of the rightmost peripheral portion). The fact that there are slits forming recesses in the outer edges of each portion ensures that each longitudinal tension indicator portion can be operated. If, in either of the three longitudinal tension indicator portions, an edge would be free of slits, i.e. no slits would reach the outer edges such that recesses are formed in the outer edges, the tension indicator would not be capable of being extended as there would be a string of material along this edge counteracting or restricting the extension of the tension indicator.

In contrast to the device shown in FIGS. 2a and 2b, the device shown in FIGS. 9a and 9b, does not comprise any intermediate portion and the tension indicator is arranged in the head portion. The device according to FIGS. 9a and 9b may however naturally be modified to comprise an intermediate portion as previously described, and if so, the tension indicator may suitably be arranged in the intermediate portion.

FIGS. 10a and 10b illustrate a top view of a part of a medical compression device according to a ninth exemplifying embodiment, before being subjected to a tension force and while being subjected to a tension force, respectively. The ninth exemplifying embodiment is similar to the device shown in FIGS. 2a and 2b with a difference in that the strip does not comprise any intermediate portion. The tension indicator 8 and the opening 9 are instead provided in the head portion 2 of the strip. Furthermore, the strip of the ninth exemplifying embodiment comprises an indicator element 40 arranged in the same plane as the rest of the strip. The indicator element 40 is connected to an outer edge 2a of the head portion, the outer edge 2a running along the longitudinal axis of the strip. The indicator element further comprises a free end 40a. The indicator element 40 is in the same plane as the head portion and bridges the tension indicator 8, and is intended to be read together with for example a scale 41 printed on a top surface of the head portion, as shown in the FIGS. 10a and 10b. In other words, the position of the free end 40a of the indicator element 40 is read in relation to the scale 41. This exemplifying embodiment has the advantage of enabling the reading of different tension forces, or the correlated levels of pressure, and may therefore be suitable in applications where different pressure may be desired depending on the situation or body part circumference. This exemplifying embodiment may however also be altered so as to provide another type of printed indicium instead of the scale, thereby enabling only one predetermined tension force of the strip to be determined. By decreasing the width of the tension indicator 8, the indicator element 40 may alternatively be fitted alongside the tension indicator without locally increasing the width of the head portion 2. Constant width of the head portion may facilitate production.

FIGS. 11a and 11b illustrate a top view of a part of a medical compression device according to a tenth exemplifying embodiment, wherein FIG. 11a illustrate a state before being subjected to tension force and FIG. 11b illustrate a state when subjected to a tension force. The tenth exemplifying embodiment corresponds to the embodiment shown in FIGS. 10a and 10b, except for the location of the indicator element 40. In the device shown in FIGS. 11a and 11b, the indicator element 40 is connected to a top surface of the head portion 2 at a first side of the tension indicator and reaches across the tension indicator longitudinally such that the free end 40a is arranged on the opposite side of the tension indicator. The free end 40a of the tension indicator functions with printed indicia, such as a scale 41, on the top surface of the strip.

FIGS. 12a and 12b illustrate a top view of a part of a medical compression device according to an eleventh exemplifying embodiment, wherein FIG. 12a illustrates a state before being subjected to tension and FIG. 12b illustrates a state when the device is subjected to the intended predetermined tension. In these figures, the tension indicator 8 is merely illustrated by wavy lines for sake of demonstration. However, in reality the tension indicator comprises a plurality of cuts provided in a predetermined pattern as previously described. The tension indicator may be planar in the plane of the strip as describes in any of the preceding exemplifying embodiments. However, it is also plausible that the tension indicator is provided in the form of a corrugated shape, undulating about the longitudinal plane of the strip.

The tension indicator 8 comprises an indicium 45 on the top surface of the tension indicator. The indicium 45 is configured to obtain a predetermined shape only when the tension indicator has been activated and extended to the intended extension, as a result of the intended predetermined tension force in the strip. FIG. 12*b* shows the strip when extended by the predetermined tension force such that the indicium 45 has acquired its intended final shape. To facilitate for the user to determine that the indicium 45 has acquired the intended shape, a reference shape 46 may also be printed in the top surface of for example the head portion 2, as shown in FIGS. 12*a* and 12*b*.

FIGS. 13*a* and 13*b* illustrate a top view of a part of a medical compression device according to a twelfth exemplifying embodiment, in a state before being subjected to a tension force and in a state when subjected to the intended tension force, respectively. The pattern of the plurality of cuts forms a plurality of meandering paths. Two such meandering paths are indicated in FIG. 13*a* by the dotted lines $M_1$, $M_2$. The cuts are in the form of circular holes 30. A first hole 30*a* of the plurality of holes 30 may optionally reach over the first outer edge 8*a* of the tension indicator 8 such that it forms a recess in the first outer edge 8*a*. Correspondingly, a second hole 30*b* of the plurality of holes 30 may optionally form a recess in the second outer edge 8*b* of the tension indicator 8. In this particular embodiment, the tension indicator 8 is designed such that when the intended tension and hence the intended compression is obtained, the width of the tension indicator conforms to the width of the head portion 2, as shown in FIG. 13*b*, thereby informing the user that the appropriate tension has been achieved. The user may then lock the strip with the intended compression by means of conventional fastening means, such as the adhesive as described with reference to FIG. 1.

FIG. 14 illustrates a top view of a medical compression device according to a thirteenth exemplifying embodiment. In this figure, the tension indicator has been omitted. The tension indicator may however be arranged anywhere in the strip as disclosed above. The medical compression device shown in FIG. 14 consists of a strip and wherein the width of the strip tapers in the loop portion 4 towards the tail portion 3. This configuration of the strip for example has the advantage of enabling the medical compression device to be used to impose a certain pressure on a body part with small circumference as well as a body part with larger circumference, while still using the same tension force. The tapered loop region corrects the area over which compression is applied, resulting in adequate pressure. While not shown in FIG. 14, the strip may naturally further comprise an intermediate portion arranged between the loop portion and the head portion as have been described with regard to previous exemplifying embodiments.

FIG. 15 illustrates a top view of a part of a medical compression device according to fourteenth exemplifying embodiment. The figure illustrates a tension indicator 8 arranged in the head portion 2. However, the tension indicator may be arranged in any portion of the device as described above. Furthermore, even though the tension indicator is shown as comprising a plurality of cuts in the form of slits, any other configuration and pattern of the cuts of the tension indicator as disclosed herein may be used. As shown in FIG. 15, the strip further comprises a limitation member 48 on each side of the tension indicator 8 and in the same plane as the tension indicator 8. Each limitation member is connected to an outer edge of the strip on either side of the tension indicator and is shaped in a curved configuration in the plane of the tension indicator. The purpose of the limitation members 48 is to ensure that the tension indicator cannot be extended to an undesirable extension, such as a pressure causing discomfort or harm to a patient. Therefore, the limitation members are intended to be straightened out when the tension indicator is activated, but avoid further extension of the tension indicator than intended. It should however be noted that during normal use of the device as intended, the limitation members 48 are not intended to be fully straightened out. They serve as an additional protection against applying an excessive pressure to the body part. The limitation members may also serve as elements that give the tension indicator more elasticity. For example, the limitation members may be configured to assist in retraction of the extended tension indicator.

A process for manufacturing the device according to the present invention may suitably comprise manufacturing a sheet or band of material and cutting the sheet or band so as to achieve the strip of the medical compression device. The strip may be produced as a single strip. However, it is also plausible to manufacture a continuous elongated band comprising a plurality of medical compression devices consisting of the strip, the strips detachably connected (for example by means of a perforation) to each other, one longitudinal end to another. Thereby, each strip can easily be separated/detached from an adjacent strip by tearing or the like by a user intending to collect a single compression device. The elongated band may suitably be provided in a box comprising an opening through which the band may run so as to enable collection of a single compression device by a user when desired. The box may be sterile. The elongated band may for example be provided in a roll inside the box or be provided in a zigzag way such that the strips of the elongated band are substantially flat inside the box and arranged on top of one another. The box and the elongated band together form a dispenser.

FIG. 16 illustrates an example of such a dispenser 50 comprising a box 51 having an opening 52 for retrieving a medical compression device from the elongated band (not shown) inside the box. The opening 52 of the box may suitably be made of firm material, possibly functionalised by metal. The box may optionally be provided with an adhesive on the bottom surface thereof, accessible by peeling off sticker backer, so as to allow the box to be secured to a surface of for example a table or the like. This facilitates single-handed retrieval of a compression medical device.

Even though preferred, the strip does not necessarily comprise an enclosed opening through which the tail portion may be passed. FIGS. 17*a* and 17*b* illustrate a medical compression device according to a fifteenth exemplifying embodiment. The tension indicator has been omitted in the figures in order to more clearly demonstrate the features intended to be specifically shown. The strip may comprise any one of the tension indicators described herein with respect to other exemplifying embodiments. Furthermore, the tension indicator may be arranged at any location along the longitudinal length of the strip as described above. The medical compression device 1 comprises a strip having a first slot 60 forming a recess in a first outer edge 61a of the strip in the head portion 2 (or an intermediate portion). The strip further comprises a plurality of second slots 62 forming recesses in a second outer edge 61b of the strip, the second slots 62 arranged in parallel and in the loop region 4. The first slot 60 is configured to be mated with one of the second slots 62 corresponding to a length of the loop portion 4 when the intended tension force has been achieved in the device 1 wrapped around a body part. The tail portion 3, or the head portion 2, may thereafter be fastened to the loop portion 4 in any conventional manner, such as by means of an adhesive (not shown). By placing the fastening mechanism so that fastening requires the longitudinal central axis of each strip end to coincide, shear stress in the pattern of the tension indicator is minimised.

Figure 18:
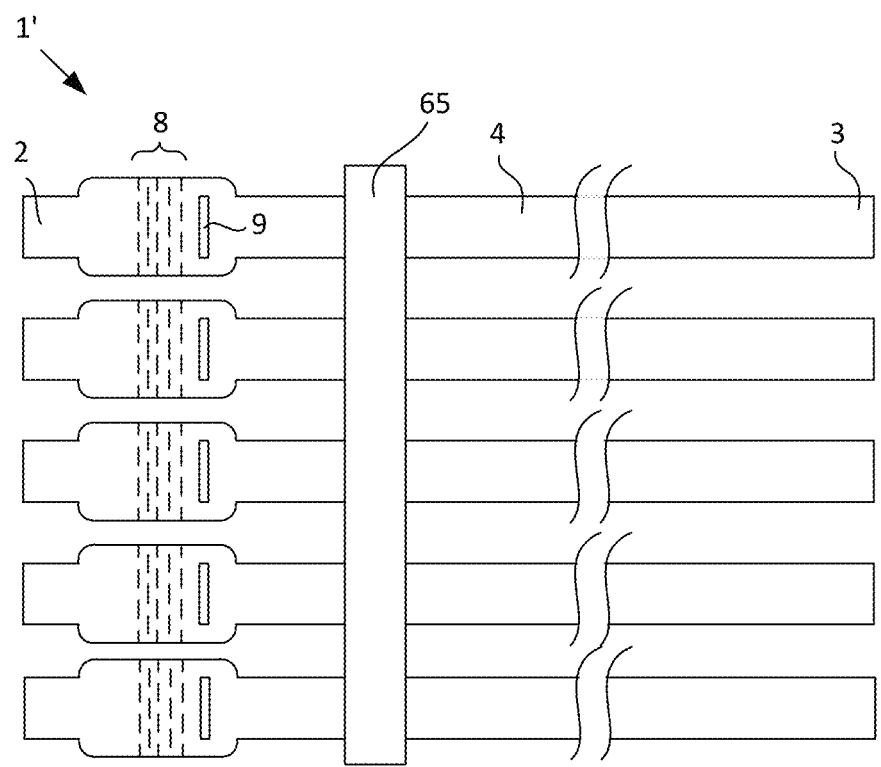

FIG. 18 illustrates a top view of a medical compression device 1' according to a sixteenth exemplifying embodiment. In contrast to previously disclosed exemplifying embodiments, the medical compression device comprises a plurality of elongated strips. The strips may be any of the previously disclosed strips. In FIG. 18, the strips are illustrated as comprising a tension indicator 8 arranged in an intermediate portion of the respective strips. The medical compression device 1' further comprises a connection member 65. The connection member 65 is configured for holding the plurality of elongated strips in a relation to one another such that the elongated strips are arranged in parallel, side by side as seen in a direction perpendicular to the longitudinal axis of each elongated strip.

Figure 19:
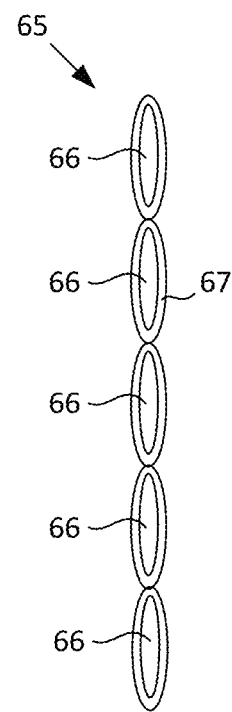
FIG. 19 illustrates a cross sectional view of a connection member of the medical compression device according to FIG. 18

FIG. 19 illustrates a cross sectional view of an example of the connection member 65. The connection member 65 is comprises walls 67 forming passages 66 through which the elongated strips may run such that the elongated strips are arranged side by side. The elongated strips are preferably arranged in the connection member such that each strip may be slid within a passage 66. The purpose of arranging the slips such that they may slide within the connection member is to facilitate use of the medical compression device by allowing the strips to be movable in relation to each other when each strip is to be tightened around a body part. In an alternate embodiment of the connection member, the passages may be simple slits arranged in series along the longitudinal length of the connection member, each slit accommodating one strip.

Figure 20:
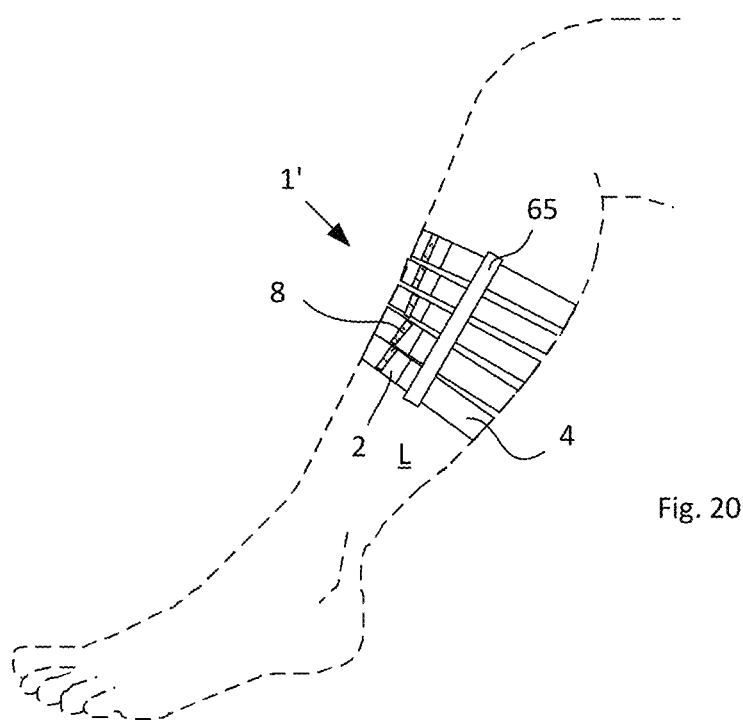
FIG. 20 illustrates a perspective view of a medical compression device as shown in FIG. 18, when wrapped around a leg.

When the medical compression device 1' is to be applied on a patient, each elongated strip is individually subjected to the intended tension force as determined by usage of the tension indicator 8. FIG. 20 illustrates a perspective view when the medical compression device has been applied to a limb L, here illustrated in the form of a leg. In the figure, the tail portion 3 is not visible since it is arranged on the other side of the leg. As can be seen in the figure, the head portion 2 overlaps with the loop portion 4 of each individual strip.

The medical compression device may for example be an arterial tourniquet. In such a case, the tension indicator is configured so that the predetermined tension corresponds to a pressure sufficient to stop arterial blood flow in the body part to which the medical compression device is applied. It will be readily understood by the skilled person that when the medical compression device is intended for such a use, the medical compression device preferably consists solely of one elongated strip, while two strips would suitably be used on the site of a proposed suture; one proximally and one distally to the site of the suture.

The medical compression device may also be used as a venous tourniquet, in which case the medical compression device suitably consists of the elongated strip. A venous tourniquet is used for intravenous (IV) access, for example when taking a blood sample or for facilitating administration of medication.

The medical compression device may further be used for diagnostics of blood pressure, in particular systolic blood pressure. In such a case, the tension indicator is configured so that the predetermined tension corresponds to a pressure on the body part correlating to a critical threshold value of systolic blood pressure. When used in such an application, the medical compression device is applied on the body part, plausibly the upper arm. When the predetermined tension has been achieved and the device is fastened so as to maintain the result pressure, the user may check whether the body part features a pulse distally with respect to the medical compression device. Thereby, the user may determine if the patient has a blood pressure below or above a critical threshold value of blood pressure. For example, in the case where the tension indicator is configured to correspond to a critical threshold value of 140 mmHg (which corresponds to high blood pressure stage 1), and the patient has a pulse in the body part after the medical compression device has been applied with the intended tension force, the user can determine that the blood pressure is above 140 mmHg. This presents an easy way to determine critical blood pressure, for example in the home, in the field or in a developing country, but also in the average clinic. Similarly, the medical compression device may be used for diagnosing hypotension by determining whether the patient has a systolic blood pressure below for example 90 mmHg where the tension indicator is adapted for such a pressure. If the patient has no pulse distally with respect to the medical compression device after the medical compression device has been applied as intended, the user receives information that the patient is suffering from hypotension. For these diagnostic purposes, the medical compression device preferably consists of one strip.

The medical compression device may furthermore be used for purposes of ensuring sufficient flow of body fluids, for example when a limb is put into a cast, so that the affected limb has the circulation necessary for proper healing. In such a case, the medical compression device may be a part of the cast, or the medical compression device may be incorporated into the cast, and may suitably comprise one or more elongated strips.

The medical compression device may further be used as a pressure dressing, bandage or wrap about an affected area for example post-operatively, at the site of burn injury or to treat the fluid build-up observed in for example lymphedema. In such cases the device suitably comprises more than one elongated strip (compare with the exemplifying embodiment shown in FIG. 18).

The material of the strip of the medical compression device according to the present invention is preferably a substantially inelastic material as previously disclosed. Such a material retains essentially the same width of the strip when subjected to a tension force, which provides a consistent correlation to pressure onto the body part during use. Pressure corresponds to force per area in contact with the limb, and therefore it is desirable to have a strip that retains the width (at least in the loop portion) when subjected to a tensile force to tighten the strip around the body part, as this aids application of certain pressure to the body part.

The medical compression device according to the present invention is not limited to the embodiments shown in the figures and discussed above, but may be varied within the scope of the appended claims.

For example, when the strip comprises an adhesive for locking the strip with the intended tension, the adhesive may be arranged on the loop portion as shown for example in FIG. 1, or alternatively, the adhesive may be arranged on the tail portion to lock against the loop portion as shown in FIGS. 7a to 7c. The adhesive may alternatively be arranged on the head portion 2 for locking against the loop portion. The adhesive may in certain instances also be arranged on the tension indicator as such. The adhesive may suitably be covered by a protective, peelable liner.

Furthermore, the adhesive may be replaced with other means for fastening while retaining the intended tension. For example, the adhesive may be replaced by hooks and loops (also known as Velcro®), which may be arranged in any of the locations described above with reference to the adhesive. It may even be plausible to use a buckle or clamp if desired, even though this is less preferred.

Moreover, the tension indicator may comprise one single meandering path of strip material between the cuts, the meandering path extending from one longitudinal end of the tension indicator to the opposite longitudinal end of the tension indicator. However, in most cases, the tension indicator comprises a plurality of meandering paths. These meandering paths may have the same or dissimilar lengths. For example, a first subset of meandering paths may have a first length and a second subset of meandering paths may have a second length different from the first length. Furthermore, the meandering paths may be parallel or non-parallel to each other. Two meandering paths adjacent to one another may be a mirror image of one another along an axis parallel to or coinciding with the longitudinal central axis of the tension indicator. Moreover, the meandering paths may have the same or different geometrical configurations compared to one another. All of the above given possibilities are a result of how the cuts in the tension indicator are arranged, and they can be adapted in accordance with the desired function of the tension indicator associated with the particular intended use of the medical compression device.

The tension indicator may be arranged in a portion of the strip that is intended not to be in direct contact with the skin of the limb to which the medical compression device is applied during use (compare for example with exemplifying embodiments shown in FIG. 1, 5a-5e, or 7a-7c). In other words, the tension indicator may be arranged in a portion of the strip adapted to overlap another portion of the strip. This inter alia has the advantage of avoiding any risk of the skin of the body part providing a frictional force that may influence the capacity of the tension indicator to extend when subjected to a tension force applied by a user. Alternatively, the tension indicator may be arranged in a portion of the strip intended to be in direct contact with the skin of the body part, for example the loop portion (compare with the exemplifying embodiment shown in FIGS. 6a and 6b).

The strip may also be provided with means for increasing the comfort of the strip during use thereof on a patient. This may for example be implemented by addition of a surface coating for reducing the friction between the strip and the skin of a patient. Furthermore, the edges of the strip may if desired be rounded, perforated or subject to alternative geometric configuration, or otherwise be subjected to a softening process. This serves to avoid the edges of the strip damaging or cutting into the skin of the patient during use. Also, the strip may have a differentially wide width in the loop portion. This would allow force distribution so that high pressure (the result of low width) would be reserved only for areas where high pressure was a medical necessity, while low pressure (the result of high width) would be used elsewhere to increase patient comfort.

Furthermore, the head portion and/or the tail portion may be provided with an anti-slip coating, perforation or protrusions to increase local friction, thereby ensuring a better grip to these portions while pulling during use of the medical compression device.

The invention claimed is:

1. A medical compression device comprising an elongated strip having a longitudinal central axis, a thickness and a width, the strip further comprising a head portion at a first longitudinal end, a tail portion at a second longitudinal end, and a loop portion arranged between the head portion and the tail portion, the loop portion having a sufficient length for encircling a body part of a human or animal, the strip further comprising means for fastening overlapping portions of the strip when the loop portion is encircling a body part applying a compression force to the body part wherein the strip comprises a tension indicator adapted to indicate when a predetermined tension in the strip along the longitudinal axis thereof has been achieved, the tension indicator having a first longitudinal end and a second longitudinal end, and comprising a plurality of cuts arranged in a predetermined pattern, wherein the pattern of the plurality of cuts forms a meandering path of the strip material present between the cuts, the meandering path extending from the first longitudinal end of the tension indicator to the second longitudinal end of the tension indicator, the plurality of cuts prohibiting a linear shortest available path through the strip material that links the first and second longitudinal ends of the tension indicator.

2. The device according to claim 1, wherein the tension indicator has a first outer edge along the longitudinal axis of the strip and an opposing second outer edge along the longitudinal axis of the strip, and wherein a first cut of the plurality of cuts forms a recess in the first outer edge and a second cut of the plurality of cuts forms a recess in the second outer edge.

3. The device according to claim 1, wherein the strip is made of substantially inelastic material.

4. The device according to claim 1, wherein the strip further comprising an opening configured for allowing the tail portion to pass through the opening so as to overlap with the head portion and/or the loop portion.

5. The device according to claim 1, wherein the strip further comprising an intermediate portion arranged between the head portion and the loop portion, wherein the strip has a greater width in the intermediate portion than in the loop portion.

6. The device according to claim 1, wherein the strip has a width in the loop portion that tapers towards the tail portion.

7. The device according to claim 1, wherein the strip comprises a first strip layer and a second strip layer superposed on the first strip layer, the tension indicator arranged in the first strip layer, and wherein the second strip layer comprises a perforation that traverses the width of the strip, said perforation arranged above the tension indicator or in the immediate vicinity thereof.

8. The device according to claim 7, wherein the second strip layer is made of a substantially inelastic material and is adhered to the first strip layer, the second strip layer comprising a plurality of the perforation traversing the width of the strip, said perforations being parallel to each other, the second strip layer comprising a plurality of removable parts each delimited by two adjacent perforations of the plurality of perforations, and wherein the first strip layer comprises a plurality of tension indicators arranged along the longitudinal axis of the loop portion, each tension indicator arranged below one of the removable parts of the second strip layer such that when a removable part of the second strip layer is removed, the tension indicator arranged below is operable while the other tension indicators are inoperable.

9. The device according to claim 8, wherein at least a first tension indicator of the plurality of tension indicators have a different Young's modulus than a second tension indicator of the plurality of tension indicators, and wherein the Young's modulus of an individual tension indicator of the plurality of tension indicators relates to the location of the individual tension indicator along the longitudinal axis of the strip.

10. The device according to claim 1, wherein the plurality of cuts comprises a plurality of slits.

11. The device according to claim 10, wherein each slit of the plurality of slits is oriented substantially perpendicular to the longitudinal axis of the strip.

12. The device according to claim 1, wherein the strip further comprises an indicium or indicia adapted to visually inform a user when at least one predetermined amount of pressure is exerted by the strip on the body part.

13. The device according to claim 12, further comprising an element attached to the strip at a first end of the element and in the vicinity of the tension indicator, the element having a free end that is adapted to move in relation to the indicium or indicia of the strip as a result of extension of the tension indicator to thereby visually inform the user when predetermined pressure is exerted by the strip on the body part.

14. The device according to claim 1, wherein the strip has a greater width in the tension indicator than in adjacent parts of the strip, and wherein the pattern of the plurality of cuts is configured to enable the width of the strip in the tension indicator to adjust to the width of the strip in adjacent parts of the strip when predetermined pressure has been achieved, so as to thereby enable a user to determine that a predetermined pressure has been achieved.

15. The device according to claim 1, wherein the tension indicator is configured so that the predetermined tension correlates to a pressure on the body part sufficient to stop arterial blood flow in the body part.

16. The device according to claim 1, wherein the tension indicator is configured so that the predetermined tension correlates to a pressure on the body part corresponding to a critical threshold value of systolic blood pressure, preferably 90 mmHg, 115 mmHg, 120 mmHg, 140 mmHg or 160 mmHg.

17. The device according to claim 1, wherein the device comprises a plurality of the elongated strip, the device further comprising one or more connection members configured for holding the plurality of elongated strips in relation to each other such that the elongated strips are arranged side by side as seen in a direction perpendicular to the longitudinal axis of each elongated strip, preferably wherein the elongated strips are arranged in the connection member such that they may be individually moved.

18. A continuous band comprising a plurality of medical compression devices according to claim 1, wherein the medical compression devices are detachably connected to each other, one longitudinal end to another.

19. A dispenser comprising a box, and a continuous band according to claim 18 contained in the box, the box comprising an opening configured for drawing out a part of the continuous band so as to reveal a medical compression device one at a time for separation from the remainder of the elongated continuous band.

* * * * *